(12) United States Patent
Choi et al.

(10) Patent No.: US 7,981,161 B2
(45) Date of Patent: Jul. 19, 2011

(54) DISPOSABLE NECK TRIAL ADAPTER

(75) Inventors: Andy Wonyong Choi, Wayne, NJ (US);
Philip Bryan, Honeoye Falls, NY (US);
Michael Bausch, Livonia, NY (US);
Scott Kennard, Brockport, NY (US)

(73) Assignee: Howmedica Osteonics Corp., Mahwah, NJ (US)

( * ) Notice: Subject to any disclaimer, the term of this patent is extended or adjusted under 35 U.S.C. 154(b) by 677 days.

(21) Appl. No.: 11/893,855

(22) Filed: Aug. 17, 2007

(65) Prior Publication Data
US 2009/0048682 A1   Feb. 19, 2009

(51) Int. Cl.
*A61F 2/32* (2006.01)
(52) U.S. Cl. ..................................... 623/22.42
(58) Field of Classification Search ............... 623/22.42, 623/23.46
See application file for complete search history.

(56) References Cited

U.S. PATENT DOCUMENTS

| | | | |
|---|---|---|---|
| 3,938,198 A | 2/1976 | Kahn et al. | |
| 4,106,128 A | 8/1978 | Greenwald et al. | |
| 4,608,055 A | 8/1986 | Morrey et al. | |
| 4,676,797 A | 6/1987 | Anapliotis et al. | |
| 4,834,758 A | 5/1989 | Lane et al. | |
| 4,921,500 A | 5/1990 | Averill et al. | |
| 4,957,510 A | 9/1990 | Cremascoli | |
| 5,002,578 A | 3/1991 | Luman | |
| 5,002,581 A | 3/1991 | Paxson et al. | |
| 5,163,961 A * | 11/1992 | Harwin ...................... | 623/22.46 |
| 5,201,882 A | 4/1993 | Paxson | |
| 5,860,982 A * | 1/1999 | Ro et al. ...................... | 606/102 |
| 5,951,606 A | 9/1999 | Burke | |
| 6,053,945 A * | 4/2000 | O'Neil et al. ............... | 623/20.32 |
| 6,336,941 B1 | 1/2002 | Subba Rao et al. | |

(Continued)

FOREIGN PATENT DOCUMENTS

EP          243298          10/1987

OTHER PUBLICATIONS

OTI, Osteoimplant Technology, Inc., Alfa II Total Hip System, Mar. 27, 2002.

(Continued)

*Primary Examiner* — Bruce E Snow
*Assistant Examiner* — Melissa Hoban
(74) *Attorney, Agent, or Firm* — Lerner, David, Littenberg, Krumholtz & Mentlik, LLP (57) ABSTRACT

The system to implant a prosthetic device in a long bone such as a femur or a humerus includes a stem implant having a recess. The system of present invention also includes a broach to prepare the long bone that may receive the stem implant. The broach also has a recess that is similar to the recess in the stem implant. An adapter of a generally rectangular shape similar to the recess fits snugly in the recess in the stem implant. A trial neck that fits snugly in the recess formed in the adapter is also provided. A trial head may be assembled on the trial neck. A neck similar to the trial neck can be inserted in place of trial neck. A head may be assembled on the proximal end of the neck. A system for implantation of a prosthetic device in a long bone may be made available as a kit that includes at least two stems having the adapter inserted in each of the stem, at least two trial necks, at least two trial heads, at least two necks and at least two heads.

13 Claims, 7 Drawing Sheets

U.S. PATENT DOCUMENTS

| | | |
|---|---|---|
| 6,428,578 B2 | 8/2002 | White |
| 6,464,728 B1 | 10/2002 | Murray |
| 6,613,092 B1 | 9/2003 | Kana et al. |
| 6,706,072 B2 | 3/2004 | Dwyer et al. |
| 6,974,483 B2 * | 12/2005 | Murray ............... 623/22.42 |
| 7,135,044 B2 | 11/2006 | Bassik et al. |
| 7,235,106 B2 | 6/2007 | Daniels et al. |
| 2002/0004685 A1 | 1/2002 | White |
| 2002/0151984 A1 | 10/2002 | White |
| 2004/0010319 A1 | 1/2004 | McTighe et al. |
| 2004/0122525 A1 * | 6/2004 | Daniels et al. ........ 623/22.42 |
| 2004/0267266 A1 * | 12/2004 | Daniels et al. ............ 606/80 |
| 2005/0143828 A1 | 6/2005 | Collins et al. |
| 2005/0203634 A1 | 9/2005 | Bassik et al. |
| 2006/0142872 A1 * | 6/2006 | Klotz et al. ............. 623/23.44 |
| 2008/0133023 A1 * | 6/2008 | Schlotterback et al. ... 623/22.42 |
| 2009/0048682 A1 | 2/2009 | Choi et al. |

OTHER PUBLICATIONS

OTI, Osteoimplant Technology, Inc., IMIN Series, Modular Femoral Necks, Mar. 27, 2002.
OTI, Osteoimplant Technology, Inc., IMIN Series, R120 Modular Total Hip System Cemented, Mar. 27, 2002.
OTI, Osteoimplant Technology, Inc., R120 Total Hip System, May 2, 2004.
1985 Spanish publication.
Symbios, SPS Modular, Apr. 2004.
Wright Medical Technology, Inc., Odyssey Tissue Preserving Initiative, Surgical Technique, 2004.

\* cited by examiner

DISPOSABLE NECK TRIAL ADAPTER

BACKGROUND OF THE INVENTION

1. Field of Invention

The present invention relates to a system for implantation of a modular prosthesis in a bone. More particularly, the present invention relates to a system wherein a single set of trial necks can be used for trial reduction of a joint using a broach and trial reduction of the joint using a stem implant.

2. Background of the Related Art

Conventional shoulder and hip prostheses typically were unitary structures including an integral stem and neck interconnecting a head. A problem associated with conventional shoulder and hip prostheses is the need to maintain large inventories of differently configured prostheses for different patient anatomies. To reduce the required inventory of parts, assorted modular prostheses have been provided. Such systems include differently sized necks, heads and necks with different lengths and angles. While existing modular prosthesis systems allow flexibility with respect to either the neck angle or the radial offset between the head and the stem to accommodate each patient's unique anatomical requirements, improvements are still needed.

In conventional modular prosthesis systems, the male feature for the neck implant for mounting on the hip or shoulder stem does not correlate with the female feature on the broach. Therefore, to allow trial reduction of a joint with both the broach and the stem implant in place, a set of trial necks for the broach and a set of trial neck for the hip or shoulder stem are required. This is in addition to a set of neck implants for the hip or shoulder stem. Thus, it would be desirable to be able to use a single set of trial neck implants with the broach and the stem implants.

The female features in the stem implants have a very fine finish and a Morse taper. The neck implant has a matching male portion with a Morse taper and locks in the female feature via assembly of the male part in the female feature of the stem implants. The quality of locking between the stem implant and the neck implant are sensitive to notching on the mating surfaces of the neck implant and the stem implant. Thus, it is desirable that the surface of the female feature of the stem implant is protected during trial reduction of the joint using the trial neck implant.

United states patent Application Publication No. 2004/0010319 (the '319 Publication) discloses a hip stem. The stem of the '319 Publication accepts necks that may be chosen from a set of modular necks. A bushing is disclosed for insertion in the female feature of the stem. The neck implant is inserted in the bushing. The bushing is implanted in the patient and provides reduction of stress and fatigue in the neck implant. The bushing is not disposable and not used to allow a single set of trial necks to be used with the stem implant and the broach.

SUMMARY OF THE INVENTION

The system of present invention includes a stem implant. A recess is formed at the proximal end of the stem implant. The recess is approximately rectangular in shape and has rounded corners. A notch is formed at the bottom of the recess. The system of present invention also includes a broach to prepare the long bone that may receive the stem implant. The broach has a recess that is similar to the recess in the stem implant. However, the recess in the broach has generally smaller sides as compared to the recess in the stem implant.

An adapter of a generally rectangular shape similar to the recess is also provided. The adapter is sized such that it fits snugly in the recess in the stem implant. Bulbous portions are formed at the distal end of the adapter. The bulbous portions are formed at the free end of two opposing cantilevered portions of the wall of the adapter. Each bulbous portion snaps into the notch formed in the recess in the stem implant when the adapter is inserted in the recess in the stem implant. The inside surface of the adapter is of approximately rectangular shape and forms a recess of a size that corresponds to the size of the recess formed in the broach. Thus, a trial neck that could fit in the recess in the broach can also fit in the recess in the stem implant with the adapter inserted in it. The adapter can be disengaged from the stem implant by using an extraction tool.

A trial neck that fits snugly in the recess formed in the adapter is also provided. A trial head may be assembled on the trial neck.

A neck similar to the trial neck is provided. The distal end of the neck is slightly larger in cross section than the distal end of the trial neck. The distal end of the neck is sized such that it will fit snugly in the recess formed in the stem implant and lock in there due to the presence of matching Morse taper on the distal end of the neck and the recess formed in the stem implant. A head may be assembled on the proximal end of the neck in the same manner as the trial head is assembled on the trial neck A system for implantation of a prosthetic device in a long bone may be made available as a kit that includes at least one stem having the adapter inserted in the stem, at least two trial necks, at least one trial head, at least two necks and at least one head.

The present system may be used to implant a prosthetic device in a long bone such as a femur or a humerus. The long bone is prepared by resecting one end of the bone and broaching the medullary canal using the broach. Once the medullary canal is prepared, the broach is left in place and the trial neck is inserted in the recess of the broach. The trial head is next assembled on the proximal end of the trial neck. Next the joint is reduced and evaluated by the surgeon. If necessary, the trial neck and the trial head are replaced by a different size trial neck and a different size trial head, and the joint reduced again. Once the reduced joint is found to be satisfactory by the surgeon, the broach, the trial neck and the trial head are removed. Next, the stem implant of the appropriate size is inserted in the medullary canal. The stem implant has the adapter inserted in the recess formed in the stem implant. The trial neck that was found to be satisfactory during the reduction using the broach is now inserted in the recess of the adapter. The trial head that was found to be satisfactory during the reduction using the broach is assembled on the proximal end of the neck. Next a trial reduction of the joint is performed and evaluated. If necessary, the trial neck and the trial head are replaced by a different size trial neck and a different size trial head. Next, the joint is reduced and evaluated. This process is repeated until the surgeon finds the reduced joint to be satisfactory. Once the surgeon is satisfied, the joint is dislocated and the trial neck, the trial head and the adapter are removed. Next, the neck that corresponds in size to the trial neck that was found to be satisfactory is impacted in the recess formed in the stem implant. Next the head that corresponds in size to the trial head that was found to be satisfactory is impacted on the proximal end of the neck.

DETAILED DESCRIPTION

Figure 1:
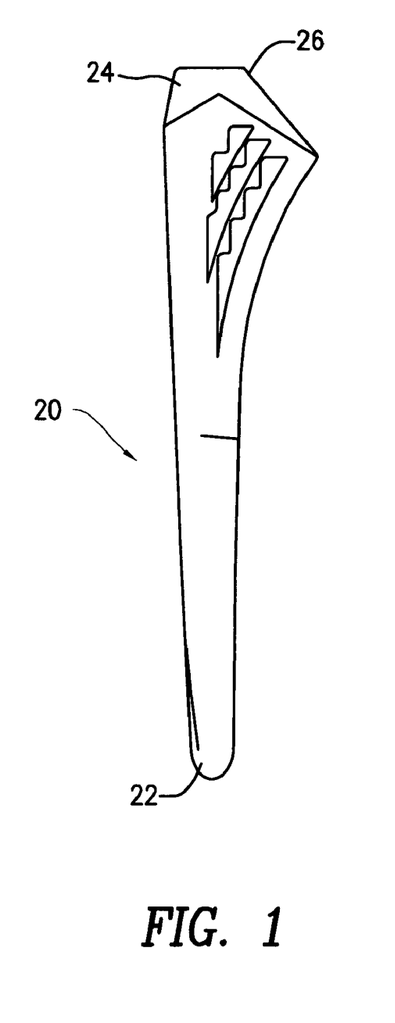
FIG. 1 is a front view of the stem implant.
Figure 2:
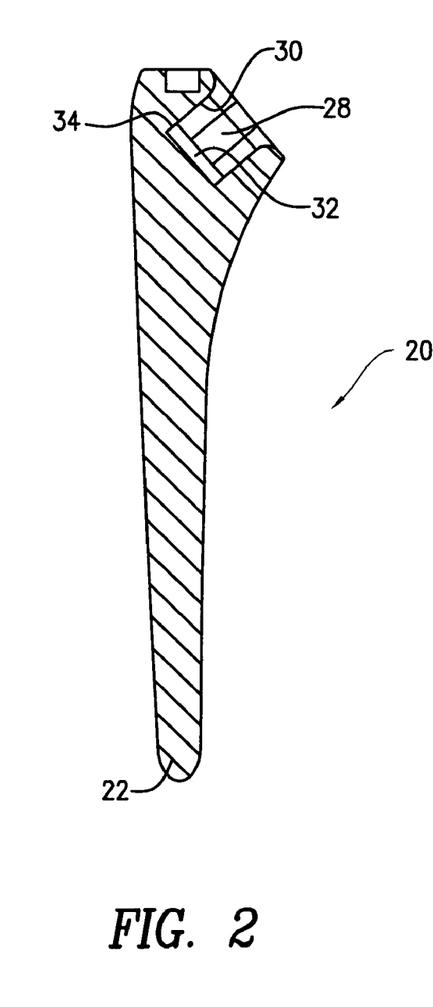
FIG. 2 is a cross sectional view of the stem implant of FIG. 1, the cross section being taken along the longitudinal axis.

FIG. 1 shows a stem implant 20. The stem implant 20 has a distal end 22 and a proximal end 24. The proximal end 24 has a face 26 that forms an angle with the longitudinal axis of the stem implant 20. FIG. 2 is a cross sectional view of the stem implant 20. The cross section shown in FIG. 2 is taken along longitudinal axis of stem implant of FIG. 1. A recess 28 is formed at the proximal end 24. The recess 28 has an opening located on the surface 26. The recess 28 is approximately rectangular in shape and has rounded corners. The recess 28 has side wall 30 formed in the body of the proximal end 24. The recess 28 has a bottom 32. The side wall 30 has a Morse taper. A notch 34 is formed where bottom 32 meets wall 30. The notch 34 is formed on sides of the rectangular recess 28. The notch 34 is formed by removing material from portions of wall 30.

Figure 3:
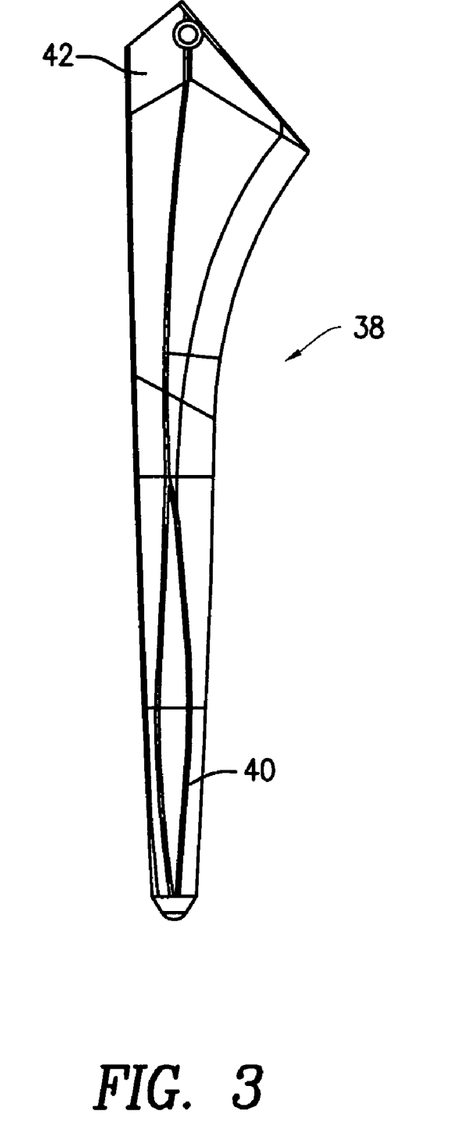
FIG. 3 is a front view of a broach.
Figure 4:
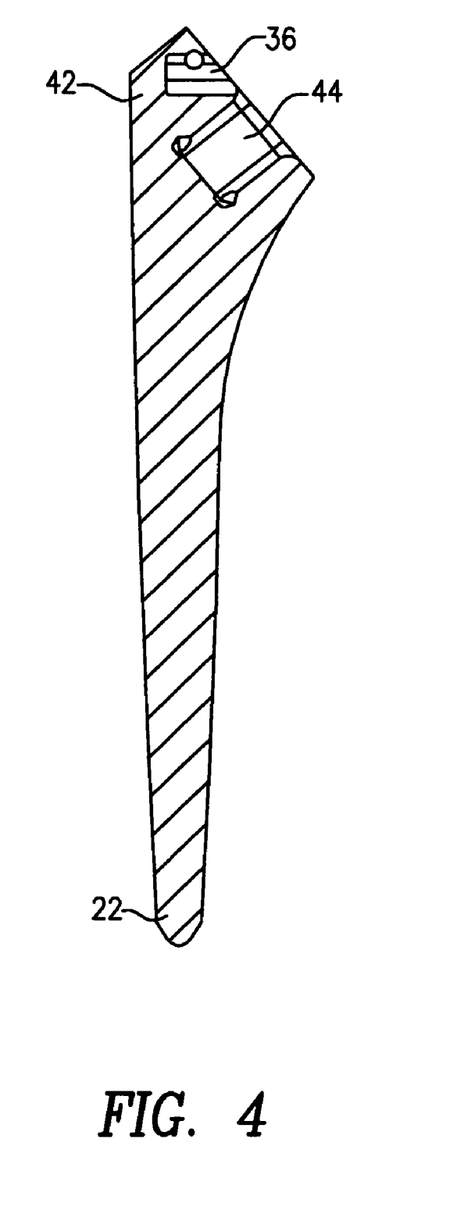
FIG. 4 is a cross sectional view of the broach of FIG. 3, the cross section being taken along the longitudinal axis of the broach.

FIGS. 3 and 4 shows a broach 38 used to prepare the long bone that may receive the stem implant 20. The broach 38 has a distal end 40 and a proximal end 42. The proximal end 42 has a recess 44 that is similar to the recess 28. However, recess 44 has generally smaller sides as compared to the recess 28. Another recess 36 is also formed on the proximal end 42 of the broach 38. The recess 36 is used to receive a hook that is used to attach a handle (not shown) to the broach 38. The handle may be used to insert and extract the broach 38 in the bone marrow. A set of the stem implants 20 of different size may be provided in a system for implanting a prosthetic device in a long bone. However, each stem implant 20 will have identical recess 28.

Figure 5:
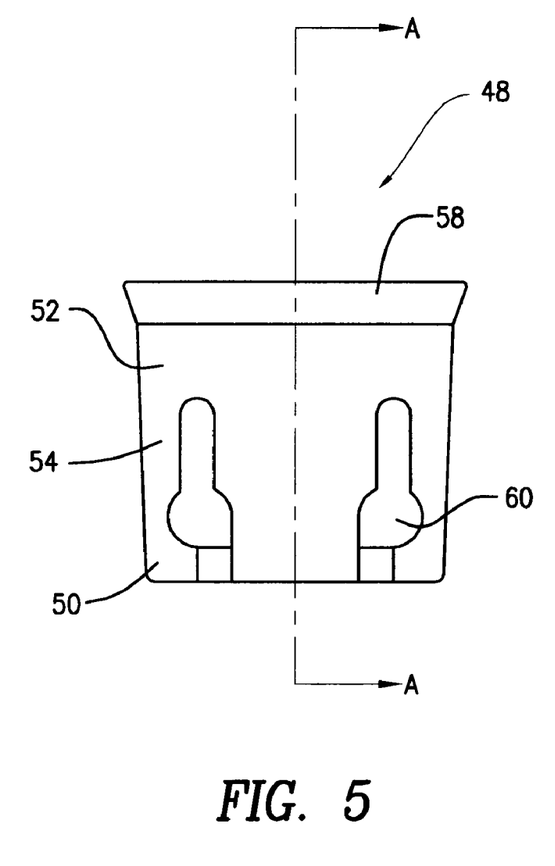
FIG. 5 is a front view of an adapter that may be inserted in the stem implant of FIG. 1.
Figure 6:
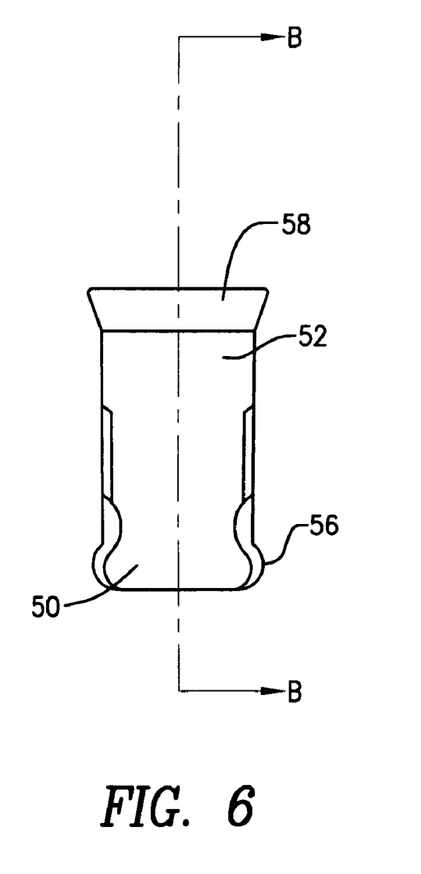
FIG. 6 is a side view of the adapter of FIG. 5.
Figure 7:
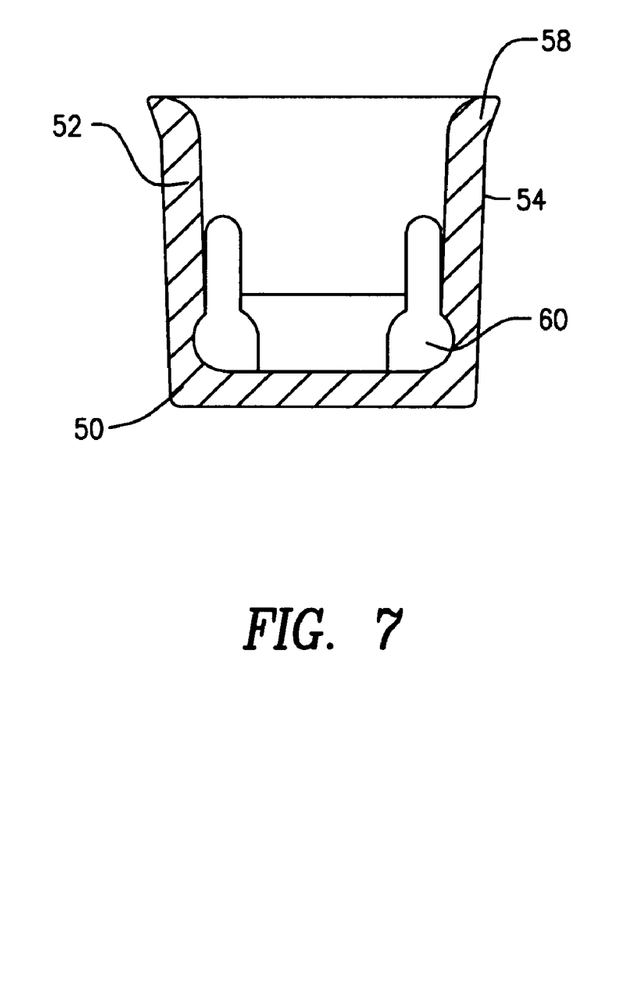
FIG. 7 is a cross sectional view of the adapter of FIG. 5 along line B-B seen in FIG. 6.
Figure 8:
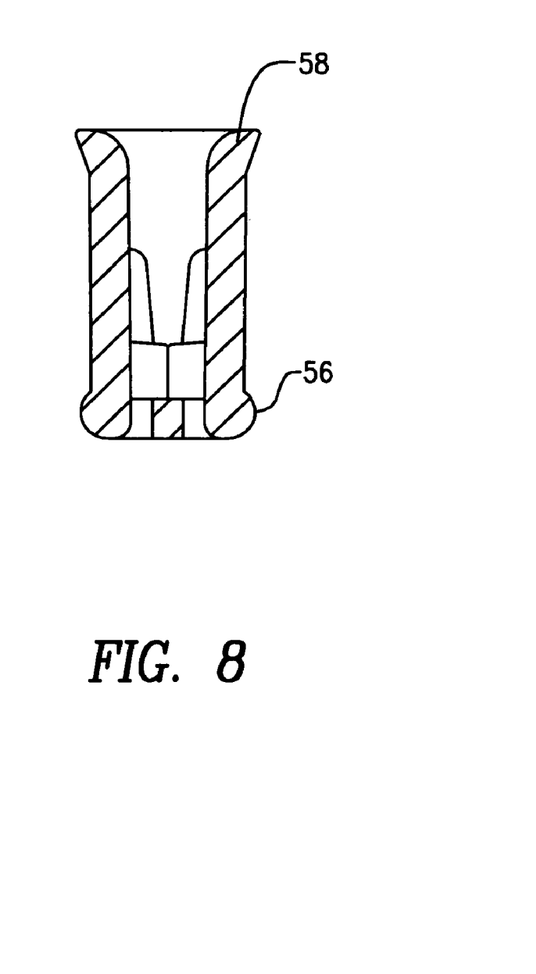
FIG. 8 is a cross sectional view of the adapter of FIG. 5 along line A-A seen in FIG. 5.

FIGS. 5 and 6 show an adapter 48. The adapter 48 has a distal end 50 and a proximal end 52. The adapter 48 has a generally rectangular shape similar to the recess 28. The adapter 48 has a wall 54 that matches the wall 30 of the recess 28. The adapter 48 is sized such that it fits snugly in the recess 28. Bulbous portions 56 are formed at the distal end 50 of the adapter 48. The bulbous portions are formed at the free end of two opposing cantilevered portions of the wall 54. Each bulbous portion 56 snaps into the notch 34 when the adapter 48 is inserted in the recess 28. A lip 58 is formed at the proximal end 52 of the adapter 48. When the adapter 48 is inserted in the recess 28, the lip 58 rests on the face 26 of the stem implant 20. FIGS. 7 and 8 show cross sectional views of the adapter 48. The inside surface of the adapter 48 is of approximately rectangular shape and forms a recess 49 of a size that corresponds to the size of the recess 44 formed in the broach 38. Thus, a trial neck 74 (FIG. 10) that could fit in the recess 44 can also fit in the stem implant 20 with the adapter 48 inserted in it. A notch 60 is formed at the distal end 50 on the inside surface of the wall 54 of the adapter 48.

Figure 9:
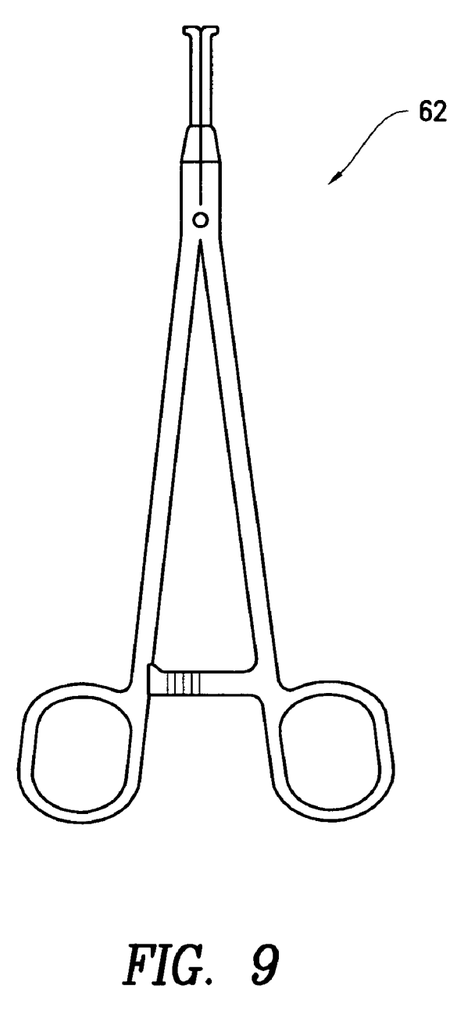
FIG. 9 is a front view of an extraction tool for extracting adapter of FIG. 5 from the stem implant of FIG. 1.

FIG. 9 shows an extraction tool 62. The extraction tool 62 is a scissor-like tool having a distal end 64 and a proximal end 66. The proximal end 66 has scissor-like hand grips 68. Upon bringing together the hand grips 68, the distal end 64 spreads apart. The distal end 64 has two arms 70 that spread apart. Distal tips 72 project away from the arms 70 to form a hook-like shape. When the extraction tool 62 is inserted in the adapter 48 that is inserted in the stem implant 20 and the two arms 70 spread apart, the distal tips 72 engage in the notch 60 formed on the inside surface of the adapter 48. The adapter 48 can be disengaged from the stem implant 20 by pulling on the extraction tool 62 with the distal tips 72 engaged in the notch 66.

Figure 10:
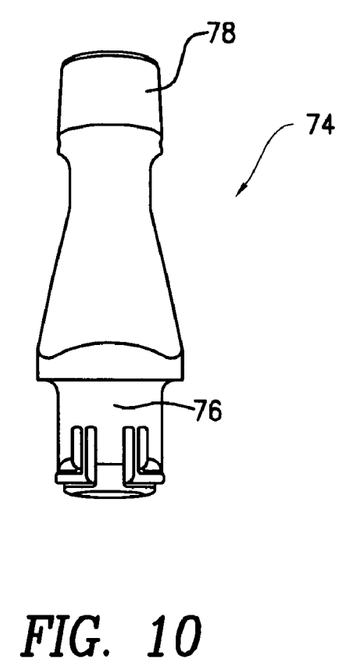
FIG. 10 is an isometric view of a trial neck for use with the stem implant of FIG. 1.
Figure 11:
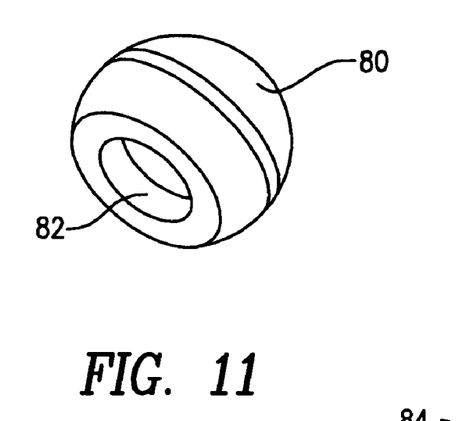
FIG. 11 is an isometric view of a trial head for use with the trial neck of FIG. 10.

FIG. 10 shows a trial neck 74. The trial neck 74 has a distal end 76 and a proximal end 78. The distal end 76 is approximately rectangular in shape and sized such that it fits snugly in the recess 44 of the adapter 48. The proximal end 78 has a Morse taper. A trial head (FIG. 11) 80 with a cylindrical opening 82 having a matching Morse taper may be assembled on proximal end 78.

Figure 12:
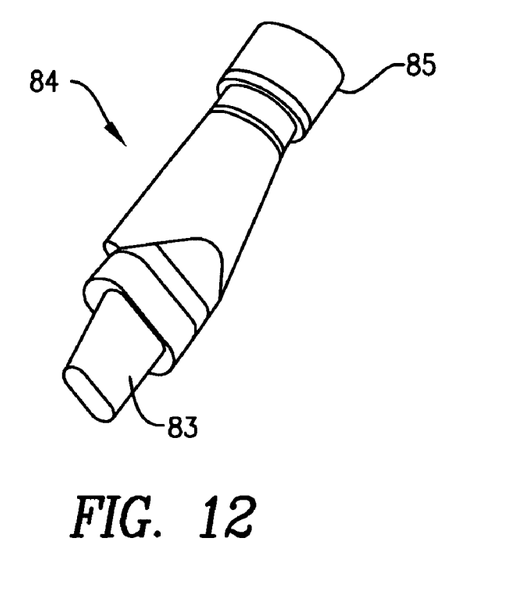
FIG. 12 is an isometric view of a neck for use with the stem implant of FIG. 1.
Figure 13:
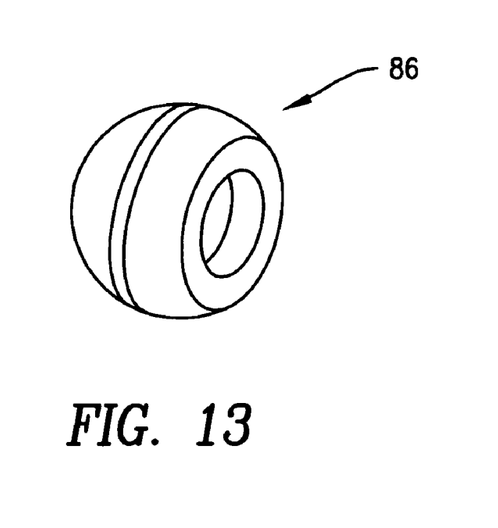
FIG. 13 is an isometric view of a head for use with the neck of FIG. 12.

FIG. 12 shows a neck 84. The construction of the neck 84 is similar to the trial neck 74 except that the distal end 83 of the neck 84 is slightly larger in cross section than the distal end of the trial neck 74. The distal end 83 of the neck 84 is sized such that it will fit snugly in the recess 28 and lock in there due to the presence of matching Morse taper on the distal end 83 of the neck 84 and the wall 30 of the recess 28. The proximal end 85 of the neck 84 is similar to the proximal end 78 of the trial neck 74. A head 86 (FIG. 13) may be assembled on the proximal end 85 of the neck 84 in the same manner as the trial head 80 is assembled on the trial neck 74.

Figure 14:
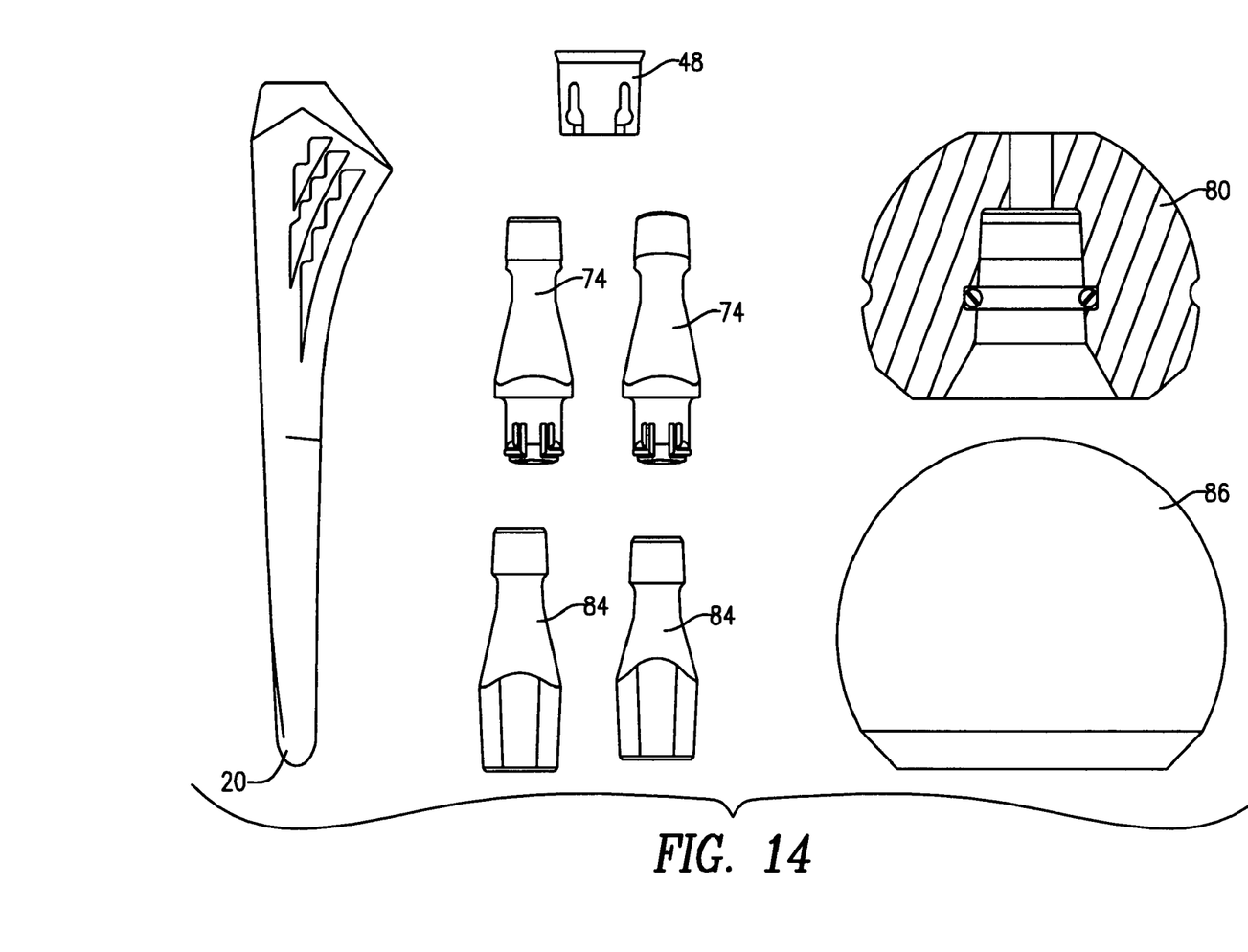
FIG. 14 shows a kit of parts that form a system for implantation of a prosthetic device in a bone.

FIG. 14 shows a kit of parts that form a system for implantation of a prosthetic device in a long bone. The kit includes at least one stem 20, adapter 48 that may be inserted in the stem 20, at least two trial necks 74, at least one trial head 80, at least two necks 84 and at least one head 86. The extraction tool 62 may also be included in the kit. The kit may contain other combinations of components as compared to the above described exemplary kit.

The present system may be used to implant a prosthetic device in a long bone such as a femur or a humerus. The long bone is prepared by resecting one end of the bone and broaching the medullary canal using the broach 38. Once the medullary canal is prepared, the broach 38 is left in place and the trial neck 74 is inserted in the recess 36 of the broach 38. The trial head 80 is next assembled on the proximal end 78 of the trial neck 74. Next the joint is reduced and evaluated by the surgeon. If necessary, the trial neck 74 and the trial head 80 are replaced by a different size trial neck 74 and a different size trial head 80, and the joint reduced again. Once the reduced joint is found to be satisfactory by the surgeon, the broach 38, the trial neck 74 and the trial head 80 are removed. Next the stem implant 20 of the appropriate size is inserted in the medullary canal. The stem implant 20 has the adapter 48 inserted in the recess 28. The trial neck 74 that was found to be satisfactory during the reduction using the broach 38 is now inserted in the recess 49 of the adapter 48. The trial head 80 that was found to be satisfactory during the reduction using the broach 38 is assembled on the proximal end 85 of the neck 84. Next a trial reduction of the joint is performed and evaluated. If necessary, the trial neck 74 and the trial head 80 are replaced by a different size trial neck 74 and a different size trial head 80. At this time the stem implant may also be replaced by a different size stem implant 20. Next, the joint is reduced and evaluated. This process is repeated until the surgeon finds the reduced joint to be satisfactory. Once the surgeon is satisfied, the joint is dislocated and the trial neck 74, the trial head 80 and the adapter 48 are removed. It should be noted that the presence of adapter 48 in the stem implant 20 during the surgery and particularly during the trial reduction protects the notch sensitive surface of recess 28. Next, the neck 84 that corresponds in size to the trial neck 74 that was found to be satisfactory is impacted in the recess 28. Next the head 86 that corresponds in size to the trial head 80 that was found to be satisfactory is impacted on the proximal end of the neck 84. Next the joint is reduced.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A system for implantation of a prosthetic device, comprising:
   a stem for implantation in a bone;
   a first recess formed in the stem having an undercut;
   a trial neck adapter having a second recess, at least one cantilevered portion, and a bulbous portion formed at an end of the cantilevered portion, the bulbous portion being adapted to fit in the undercut in the first recess, the undercut being adapted to removably lock the trial neck adapter, the trial neck adapter adapted for insertion in and removal from the first recess;
   a trial neck adapted for insertion in the second recess; and
   a neck adapted for insertion in the first recess after removal of the trial neck and the trial neck adapter.

2. The system of claim 1, further comprising:
   a trial head, the trial head adapted to mount on the trial neck.

3. The system of claim 2, further comprising:
   a head adapted for insertion on the neck.

4. The system of claim 3, wherein the trial neck adapter is made from a biocompatible medical grade plastic.

5. The system of claim 3, wherein the first recess is substantially rectangular.

6. The system of claim 3, wherein the first recess has a Morse taper.

7. The system of claim 3, wherein the first recess is adapted to taper lock the neck.

8. The system of claim 3, wherein the neck has a first end for engagement with the first recess and a second end for mounting the head, the second end having a taper suitable for taper locking the head on the neck.

9. The system of claim 3, wherein the head has a tapered bore, the taper being configured to taper lock the head on the neck.

10. A system for implantation of a prosthetic device, comprising:
    a broach for preparing a bone cavity;
    a first recess formed in the broach;
    a stem for implantation in a bone;
    a second recess formed in the stem having an undercut;
    a trial neck adapter insertable in the second recess and having a third recess, at least one cantilevered portion, and a bulbous portion formed at an end of the cantilevered portion, the bulbous portion being adapted to fit in the undercut in the second recess, the undercut being adapted to removably lock the trial neck adapter;
    a trial neck adapted for insertion in the first recess and the third recess; and
    a neck adapted for insertion in the second recess.

11. The system of claim 10, further comprising:
    a trial head, the trial head adapted to mount on the trial neck.

12. The system of claim 11, further comprising:
    a head adapted for insertion on the neck.

13. The system of claim 10, wherein the trial neck adapter is adapted for removal from the second recess.

* * * * *

UNITED STATES PATENT AND TRADEMARK OFFICE
CERTIFICATE OF CORRECTION

| | | |
|---|---|---|
| PATENT NO. | : 7,981,161 B2 | |
| APPLICATION NO. | : 11/893855 | |
| DATED | : July 19, 2011 | |
| INVENTOR(S) | : Andy Wonyong Choi et al. | |

It is certified that error appears in the above-identified patent and that said Letters Patent is hereby corrected as shown below:

Title Page, Item (74) Attorney, Agent, or Firm – please change the name "Krumholtz" to read --Krumholz--.

Signed and Sealed this
Tenth Day of July, 2012

David J. Kappos
*Director of the United States Patent and Trademark Office*